United States Patent [19]

Murayama et al.

[11] Patent Number: 5,229,211
[45] Date of Patent: Jul. 20, 1993

[54] MEDICAL DEVICE FOR INSERTION INTO A BODY

[75] Inventors: Hiraku Murayama; Naofumi Okajima, both of Fujinomiya, Japan

[73] Assignee: Terumo Kabushiki Kaisha, Shibuya, Japan

[21] Appl. No.: 770,327

[22] Filed: Oct. 3, 1991

[30] Foreign Application Priority Data

Oct. 4, 1990 [JP] Japan ................................ 2-267025

[51] Int. Cl.$^5$ ...................... B32B 27/08; A61M 25/00
[52] U.S. Cl. ............................ 428/424.4; 428/475.2; 428/482; 428/483; 428/518; 604/8; 604/280
[58] Field of Search .................. 428/424.4, 475.2, 482, 428/483, 518

[56] References Cited

FOREIGN PATENT DOCUMENTS

| | | |
|---|---|---|
| 0106004 | 4/1984 | European Pat. Off. . |
| 0166998 | 1/1986 | European Pat. Off. . |
| 59-81341 | 5/1984 | Japan . |
| 1-33181 | 7/1989 | Japan . |
| 1-195863 | 8/1989 | Japan . |
| 2112646 | 7/1983 | United Kingdom . |
| 2206118 | 12/1988 | United Kingdom . |

*Primary Examiner*—P. C. Sluby
*Attorney, Agent, or Firm*—Burns, Doane, Swecker & Mathis

[57] ABSTRACT

A medical device for insertion into a body, wherein a part of a substrate thereof destined to be inserted into the body is furnished with a coating of a polymer manifesting lubricity in a wetted state and a part of said substrate destined substantially not be inserted into the body is furnished with said polymer coating treated for divestiture of lubricity.

8 Claims, 1 Drawing Sheet

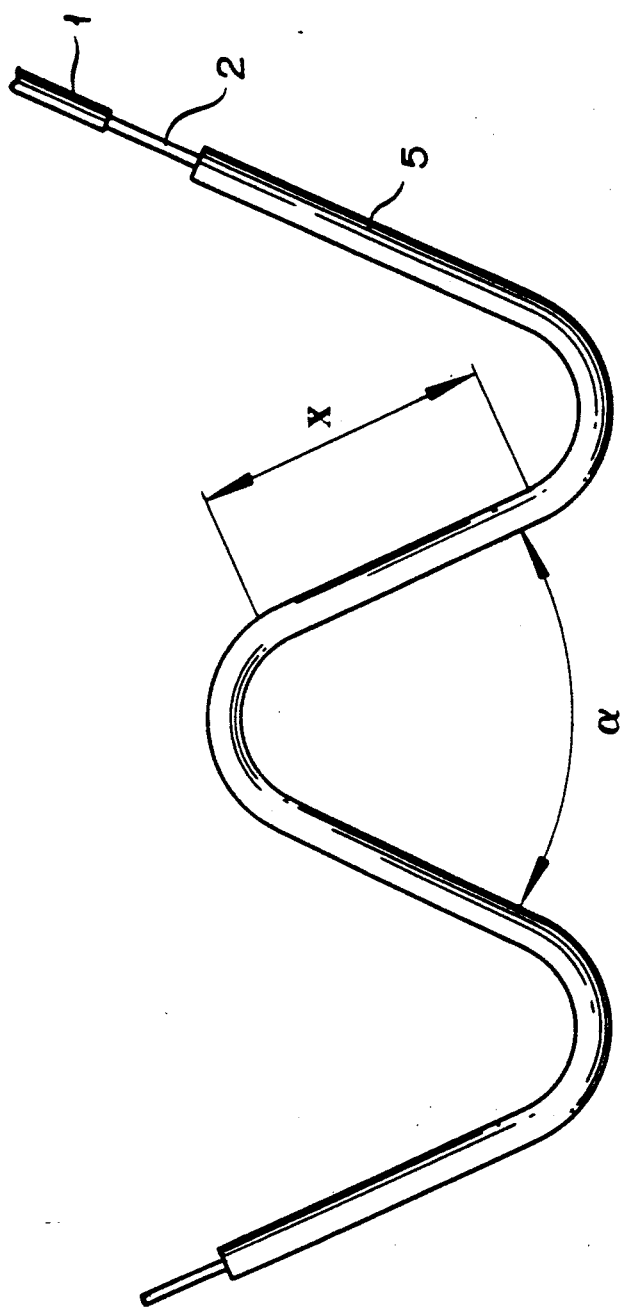

MEDICAL DEVICE FOR INSERTION INTO A BODY

BACKGROUND OF THE INVENTION

1. Field of the Invention

This invention relates to a medical device. More particularly, it relates to a medical device for insertion into a body, which medical device is plunged into the body tissue with only slight resistance.

2. Description of the Prior Art

Various medical devices including medical devices such as catheters which are inserted into a respiratory tract, a windpipe, a digestive tract, an urethra, a blood vessel, other body cavity, and body tissues and medical devices such as guide wires and stylets which are passed through the catheters and plunged into the body tissues are required to possess smoothness enough to attain insertion infallibly to the region aimed at without inflicting any damage on the tissues. Further, they are required to manifest ideal lubricity enough to avoid inflicting damage on mucous membranes due to friction during their retention in the tissues and consequently inducing inflammation of the affected part.

To satisfy these requirements, a method for treating the surface of a substrate of a medical device for insertion into the body with a hydrophilic polymer adapted to form an unreacted isocyanate group intended to be joined by a covalent bond to the surface of the substrate (JP-A-59-81,341), a medical device so constructed that the reactive functional group present at least on the surface of the substrate of the medical device is caused to form a covalent bond with such a water-soluble polymer as a cellulosic polymeric substance, polyethylene oxide, or water-soluble polyamide or a derivative of the water-soluble polymer and consequently the surface, on being wetted, is allowed to assume lubricity (JP-A-1-195,863), and a medical device which is so constructed that the reactive functional group present at least on the surface of the substrate of the medical device is caused to form a covalent bond with a maleic anhydride containing polymer and consequently the surface, on being wetted, is allowed to assume lubricity (JP-B-1-33,181) have been proposed.

When the entire surface of the substrate is coated with a hydrophilic polymer, however, the part of the medical device inserted in the body offers decreased frictional resistance and, at the same time, the basal part of the medical device reamining outside the body and serving as a manipulating part offers similarly decreased frictional resistance and manifests high slipperiness and degraded manipulatableness. Thus, the medical device using this coating necessitates use of a special adapter designed to facilitate the manipulation thereof.

The substrate of the medical device of this kind by its nature is required to have a flat smooth surface for the sake of improvememen in antithrombosis. The basal manipulating part of the medical device left outside the body, on being wetted with moisture such as blood, is deprived of the frictional resistance by the moisture possibly to a point where slipperiness is aggravated and manipulatableness is degraded.

For the purpose of overcoming this inferior manipulatableness, it suffices to have only the necessary part of such medical device as a catheter or a guide wire for a catheter coated with a hydrophilic and wettable resin. An attempt at partially forming the coating as by dipping, however, entails a sacrifice of the uniformity of the produced coating.

An object of this invention, therefore, is to provide a novel medical device.

Another object of this invention is to provide a medical device for insertion in the body, which medical device encounters decreased resistance to the slide thereof during the insertion in the body and enjoys improved manipulatableness while suffering no sacrifice of slidableness.

SUMMARY OF THE INVENTION

These objects are accomplished by a medical device for insertion in the body, wherein a part of the substrate to be inserted into a body is provided with a polymer coating exhibiting lubricity while in a wet state and a part of the substrate to be left substantially outside the body is provided with the same polymer coating as described above except this polymer coating has undergone a treatment for disruption of lubricity.

This invention discloses a medical device, wherein the polymer coating mentioned above is made of a hydrophilic compound or a derivative thereof. This invention also discloses a medical device, wherein the hydrophilic compound mentioned above is a maleic anhydride containing polymer. This invention further discloses a medical device, wherein the treatment to be performed on a polymer coating for the disruption of lubricity uses an isocyanate compound. This invention discloses a medical device, wherein the polymer coating mentioned above forms a covalent bond with a reactive functional group present on the surface of the substrate.

The medical device such as a catheter according to this invention enjoys notably improved manipulatableness because the part thereof to be inserted in the body offers small frictional resistance and attains the insertion thereof in the body with ease and the basal part thereof offers larger frictional resistance than any medical tool which has not undergone the treatment contemplated by this invention.

BRIEF DESCRIPTION OF THE DRAWING

The figure is a front view illustrating a method for testing resistance to insertion for the confirmation of the effect of this invention.

EXPLANATION OF THE PREFERRED EMBODIMENT

Now, the concrete construction of the present invention will be described in detail below.

For the formation of a lubricant polymer coating for the medical device of this invention, a water-soluble polymeric compound is preferably used as the material for the coating and to be fixed on a substrate of the medical device by virtue of a covalent bond. The hydrophilic polymeric compounds which are effectively usable for this purpose are linear non-crosslinked polymeric substances which have such hydrophilic groups as $-OH$, $-CONH_2$, $-COOH$, $-NH_2$, $-COO^-$, $-SO_3^-$, and $-NR_3^+$, for example. When the compounds are water soluble, it is necessary to insolubilize in water after coating the water-soluble polymeric compounds on the substrate.

As such water-soluble polymeric compounds, there are following compounds:

Natural water-soluble polymeric compounds which are usable herein include (1) starch compounds such as carboxymethyl starch and dialdehyde starch, (2) cellulosic, compounds such as carboxymethyl cellulose, methyl cellulose, hydroxyethyl cellulose, and hydroxypropyl cellulose, (3) tannin and lignin compounds such as tannin and lignin, (4) polysaccharide compounds such as alginic acid, gum arabic, guayule rubber, tragacanth gum, and tamarind seed, and (5) proteins such as gelatin, casein, glue, and collagen, for example. Synthetic water-soluble polymers which are usable herein include (1) PVA polymers such as polyvinyl alcohol, (2) polyethylene oxide polymers such as polyethylene oxide and polyethylene glycol, (3) acrylic acid polymers such as sodium polyacrylate and acrylic acid-sodium acrylate copolymer, (4) maleic anhydride containing polymers such as methyl vinyl ether-maleic anhydride copolymer, (5) phthalic acid polymers such as polyhydroxyethyl phthalic esters, (6) water-soluble polyesters such as polydimethylol propionic esters, (7) ketone aldehyde resins such as methylisopropyl ketone and formaldehyde resin, (8) acrylamide polymers such as polyacryl amide, (9) polyvinyl pyrrolidones such as PVP, (10) polyamines such as polyethylene imine and polypropylene imine, (11) polyelectrolytes such as polystyrene sulfonate, and (12) other polymers such as water-soluble polyamides, for example.

Among other water-soluble macromolecular compounds cited above, maleic anhydride polymers, cellulosic polymeric compounds, polyethylene oxide polymeric compounds, and water-soluble polyamides prove to be particularly desirable in point of high and lasting lubricity in their wet state.

The effect of the coating is prominent when a maleic anhydride containing polymeric compound is used as the polymer. In this case, the maleic anhydride containing polymeric compound may be a homopolymer or a copolymer of maleic anhydride. Among other maleic anhydride containing polymeric compounds which are favorably usable herein, a partial-alkyl (C1 to C4) ester of a methyl vinyl ethermaleic anhydride copolymer proves to be particularly preferably. As a typical example of this ester, a substantially equimolar (1:1) copolymer marketed by G.A.F. Corporation under trademark designation of "GANTREZ AN" may be cited.

The term "derivative of the water-soluble compound" as used in this invention is not meant to exclude water-soluble derivatives. The derivatives effectively usable herein have no particular restriction except for the requirement that they should possess the water-soluble polymeric substances as backbones. Even an insolubilized derivative of the water-soluble substance is acceptable on the condition that it should possesses freedom in point of molecular chain as described more specifically hereinbelow and should be capable of hydration. The derivatives of water-soluble compounds which are usable effectively herein include esterification products, salts, amidation products, anhydride, halogenation products, etherification products, hydrolyzates, acetalization products, hydroformylation products, hydroalkylation products, quaternization products, diazotization products, products of conversion into hydrazines, sulfonation products, vitrification products, and ion complexes obtained by condensation, addition, substitution, oxidation, and reduction of the aforementioned water-soluble polymeric compounds; products of cross-linking of the water-soluble polymeric compounds with substances possessing at least two reactive functional groups such as of diazonium, azide, isocyanate, acid chloride, acid anhydride, imino-carbonic ester, amino, carboxyl, epoxy, hydroxyl, and aldehyde groups; and copolymers of water-soluble polymeric compounds with vinyl compounds, acrylic acid, methacrylic acid, dine type compounds, and maleic anhydride, for example.

When a water-soluble polymeric compound of the description given above is thoroughly dissolved in water, the resultant aqueous solution is insolublized on the substrate and it can be used as a lubricant as evidenced by the fact that this insolubilized hydrophilic polymeric compound, when interposed between opposed objects of a certain substance, serves to lower conspicuously the frictional resistance which would exist otherwise between the opposed surfaces of the object.

The derivative obtained by subjecting this water-soluble polymeric compound to condensation, addition reaction, or substitution reaction or the derivative resulting from partial cross-linking of the water-soluble polymeric compound can be also used effectively as a lubricant.

A lubricant layer deposited on a base material can be obtained by causing the water-soluble polymeric compound or the derivative mentioned above to form a covalent bond with the reactive functional group existing inherently in the substrate or on the surface of the substrate or incorporated preparatorily therein. The lubricant surface thus produced persists for a long time in spite of the action of water.

The water-soluble polymeric compound is not particularly restricted by its average molecular weight. It is, however, preferable to have an average molecular weight approximately in the range of from 10,000 to 5,000,000, preferably from 40,000 to 100,000, to produce a lubricant layer which possesses high lubricity and a proper thickness and avoids manifesting conspicuously high swellability in a hydrated state.

The reactive functional group which inherently exists in the substrate or on the surface thereof or which is incorporated preparatorily therein has no particular restriction except for the requirement that it should react with the water-soluble polymeric compound and fix itself by dint of bonding or cross-linking. The reactive functional groups which are effective in this respect include diazonium group, azide group, isocyanate group, acid chloride group, acid anhydride group, imino-carbonic ester group, amino group, carboxyl group, epoxy group, hydroxyl group, and aldehyde group, for example. Among other reactive functional groups mentioned above, isocyanate group, amino group, aldehyde group, and epoxy group prove to be particularly preferable.

Preferable reactive functional group-containing substrate, therefore, are polyurethane and polyamide, for example.

The substrates used for forming the outer wall, inner wall, etc. of various medical devices may or may not contain such a reactive functional group as mentioned above. When the substrate contains no reactive functional group, it is treated with a substance possessing a reactive functional group and consequently made to incorporate this reactive functional group therein and eventually allowed to form a covalent bond with a water-soluble polymeric compound to be deposited thereon through the medium of this reactive functional group. Though the bonding is attainable in various forms such as covalent bond, ionic bond, and physical adhesion, the covalent bond is most preferable in point of ability to persist.

The reactive functional group-containing compounds which are effectively usable herein include polyisocyanates such as ethylene diisocyanate, hexamethylene diisocyanate, xylene diisocyanate, toluene diisocyanate, diphenyl methane diisocyanate, naphthalene diisocyanate, diphenyl methane diisocyanate, phenylene diisocyanate, cyclohexylene diisocyanate, triphenylmethane triisocyanate, and toluene triisocyanate, adducts and prepolymers of these polyisocyanates with polyols, for example. They further include low molecular polyamines such as ethylene diamine, trimethylene diamine, 1,2-diaminopropane, tetramethylene diamine, 1,3-diaminobutane, 2,3-diaminobutane, pentamethylene diamine, 2,4-diaminopentane, hexamethylene diamine, octamethylene diamine, nonamethylene diamine, decamethylene diamine, undecamethylene diamine, dodecamethylene diamine, tridecamethylene diamine, octadecamethylene diamine, N,N-dimethyl ethylene diamine, N,N-diethyl trimethylene diamine, N,N-dimethyl trimethylene diamine, N,N-dibutyl trimethylene diamine, N,N,N'-triethyl ethylene diamine, N-methyl trimethylene diamine, N,N-dimethyl-p-phenylene diamine, N,N-dimethyl hexamethylene diamine, diethylene thiamine, triethylene tetramine, tetraethylene pentamine, heptaethylene octamine, nonaethylene decamine, 1,3-bis(2'-aminoethylamino) propane, bis(3-aminopropanol)amine, 1,3-bis(3'-aminopropylamino) propane, 1,2,3-triaminopropane, tris(1-aminoethyl)amine, terra(aminomethyl) methane, methyl iminobispropylamine, methyl iminobisethylamine, ethyl iminobisethylamine, N-aminopropyl-2-morphorine, N-aminopropyl-2-pipecoline, N-(2-hydroxyethyl) trimethylene diamine, xylylene diamine, phenylene diamine, piperazine, N-methyl piperazine, N-(2-aminoethyl) ethanolamine, N-aminoethyl piperazine, N,N,N',N'-tetramethyl ethylenediamine, and N,N,N',N',-tetramethyltetramethylene diamine, for example. They further include macromolecular polyamides such as (I) poly(alkylenepolyamines) synthesized from amines and alkylene dihalides or epichlorohydrin (Encyclopedia of Polymer Science and Technology, Vol. 10, page 616), (II) alkylene imine polymers obtained by ring-opening polymerization of such alkylene imines as ethylene imine and propylene imine (Encyclopedia of Polymer Science and Technology, Vol. 1, page 734), and (III) polyamines such as polyvinyl amine and polylysine, for example.

The reactive functional group-containing compounds further include polyaldehydes such as glutaraldehyde, terephthalaldehyde, isophthalaldehyde, dialdehyde, starch, glyoxal, malonaldehyde, succinic acid aldehyde, adipaldehyde, pimelin dialdehyde, suberin dialdehyde, malein aldehyde, and 2-pentene-1,5-dialdehyde, for example. They also include polyepoxides such as ethylene glycol diglycidyl ether, polyethylene glycol diglycidyl ether, propylene glycol diglycidyl ether, polypropylene diglycidyl ether, hexanediol diglycidyl ether, and trimethylolpropane triglycidyl ether, for example.

Among other reactive functional group-containing compounds mentioned above, adducts of 4,4'-diphenyl methane diisocyanate and tolylene diisocyanate with trimethylolpropane, an adduct of hexamethylene diisocyanate with trimethylolpropane, trimers thereof, and diethylene triamine prove to be most preferable.

In the present invention, the substrate to be used is restricted very little by the kind of substance. The substances which are usable for the substrate include various organic polymeric compounds such as polyamides, polyesters (represented by polyethylene terephthalate and polystyrene terephthalate), polyvinyl chloride, polystyrene, polyacrylic esters, polymethacrylic esters, polyacrylonitrile, polyacrylamide, polyacrylic acid, polymethacrylic acid, polyethylene, polypropylene, polyvinyl alcohol, polymaleic anhydride, polyethylene imine, polyurethane, polyvinyl acetate, silicone resins, various latexes, and various copolymers and blends thereof, and various inorganic and metallic substances such as glass, ceramics, stainless steel, and a super elastic metal or shape memory alloy such as Ni-Ti alloy, for example. The shape of the substrate to be used are rod-like, wire and tubular shape.

Optionally, the substance to be used for the substrate may incorporate therein various additives.

Among other substances mentioned above, the organic polymers particularly feature the ability to retain the lubricity for a long time. In all the organic polymers, those of the polyvinyl chloride type, polyurethane type, polyamide type, latex type, and polyester type are most effective in manifesting this ability.

When the substrate is made of other resin or a metal or glass, for example, the medical device aimed at by this invention is obtained by preparatorily forming on the surface of this base material a layer of the same organic polymer resin as used on the aforementioned substrate and subsequently forming a lubricant layer by introducing therein or blending therewith a reactive functional group.

The formation of the resin coating on the substrate of this invention is accomplished as follows.

Where an ordinary substrate containing no reactive functional group is used, an undercoating layer is preferably formed as a preparatory step. The formation of this undercoating layer is effected by immersing the substrate in a solution containing a compound possessing such a reactive functional group as described above and subsequently drying the substrate wetted with the solution.

The solvents which are usable in the preparation of the solution for this immersion include ketones such as methylethyl ketone, methylisobutyl ketone, and cyclohexanone, esters such as butyl acetate, ethyl acetate, carbitol acetate, and butyl carbitol acetate, ethers such as methyl cellosolve, ethyl cellosolve, and tetrahydrofuran, aromatic compounds such as toluene and xylene, halogenated alkyl compounds such as dichloroethane, and alcohols, for example.

The solvent to be used for this purpose is preferably capable of dissolving or swelling the substrate made of resin in particular (which may be occasionally a coating layer of resin formed preparatorily on the surface of the aforementioned base material). This quality of the solvent enhances the adhesive strength of the coating layer and adds to the lasting effect of lubricity.

Among the solvents cited above, methylethyl ketone, cyclohexane, tetrahydrofuran, xylene, and methyl alcohol particularly prove to be ideal in this respect.

For the application of the undercoating layer to the substrate, such techniques as brushing and spinner coating are available besides the treatment of immersion mentioned above.

The subsequent drying step is intended to effect diffusion of the solvent by vaporization from the applied layer of the solution into the ambient air. Generally, this drying carried out at a temperature approximately in the range of from 20° to 80° C., preferably from 30° to 50° C. for a period approximately in the range of from 5 minutes to 48 hours, preferably from 10 minutes to 1 hour, suffices for the purpose.

Where an adhesive layer is deposited on the surface of the substrate as described above, this deposition may be accomplished by the conventional procedure.

Subsequently, the substrate on which the undercoating layer has been formed (optionally with the omission of the formation of an undercoating layer) is treated with a solution containing a water-soluble polymeric substance of the present invention. The solvent to be used for the preparation of this solution is preferably incapable of reacting with the reactive functional group, specifically an isocyanate group or amino group, which is present in the base material or the adhesive layer. Particularly, it is preferable to be methylethyl ketone, tetrahydrofuran, or acetone, for example. Ideally, this solvent is capable of dissolving or swelling the base material. The concentration of this solvent is approximately in the range of from 0.1 to 15%, preferably from 0.5 to 10%.

The treatment is generally effected by immersing the substrate in the same manner as described above. Besides the immersion, various coating methods are available for this treatment. The treating temperature is approximately in the range of from 20° to 80° C., preferably from 30° to 50° C. and the treating time approximately in the range of from 1 second to 48 hours, preferably from 1 second to 1 hour.

The subsequent drying may be carried out satisfactorily at a temperature approximately in the range of from 20° to 80° C., preferably from 40° to 60° C. for a period approximately in the range of from 5 minutes to 48 hours, preferably from 10 minutes to 1 hour.

In consequence of the procedure described above, the water-soluble polymeric compound of the present invention forms a coating layer by dint of covalent bond with a reactive functional group. The thickness of the coating layer thus formed is in the range of from 1 to 10 $\mu$m, preferably from 2 to 5 $\mu$m, on dry basis.

In the present invention, the coating layer formed as described above may be subjected to a water treatment which is disclosed in JP-B-1-33181, for example. Generally, this water treatment is accomplished simply by immersing the coating layer in water and then drying the coating layer wetted with the water. In this case, the immersing time is in the range of from 10 minutes to two hours, preferably from 30 to 60 minutes and the drying is carried out at a temperature in the range of from 25° to 80° C., preferably from 30° to 60° C. for a period of from 0.5 to 48 hours, preferably from 1 to 24 hours. Optionally, this water treatment may be effected otherwise by steam treatment.

In the medical device of this invention furnished as described above with the lubricant resin coating, the basal manipulating part thereof which is not inserted into the body is subjected to a treatment for the divestiture of lubricity. This divesting treatment is ideally carried out particularly by the use of an isocyanate compound. The isocyanate compound is thought to divest the water-soluble polymeric compound of lubricity by being grafted thereto or inducing partial crosslinking thereof. The isocyanate compounds which are effectively usable for this treatment include poly- or mono-isocyanates such as ethylene diisocyanate, hexamethylene diisocyanate, xylene diisocyanate, toluene diisocyanate, diphenyl methane diisocyanate, naphthalene diisocyanate, diphenyl methane diisocyanate, phenylene diisocyanate, cyclohexylene diisocyanate, triphenyl methane triisocyanate, and toluene triisocyanate, adducts of these polyisocyanates with polyols, and prepolymers thereof, for example.

The treatment for the divestiture of lubricity is carried out by immersing the necessary part of the base material furnished with the resin coating in a solution containing an isocyanate compound and thereafter drying the consequently wet part.

The solvents which are effectively usable in the preparation of the solution for this immersion include ketones such as methylethyl ketone, methylisobutyl ketone, and cyclohexanone, esters such as butyl acetate, ethyl acetate, carbitol acetate, and butyl carbitol acetate, ethers such as methyl cellosolve, ethyl cellosolve, and tetrahydrofuran, aromatic compounds such as toluene and xylene, and halogenated alkyl compounds such as dichloroethane, for example.

The isocyanate compound concentration in this solution is preferable to be approximately in the range of from 0.1 to 10%, preferably from 0.5 to 5%. The immersing time is approximately in the range of from 0.1 to 30 seconds, preferably from 1 to 15 seconds. After the immersion, the substrate wetted with the solution is dried to expel the solvent by vaporization. Generally, the drying temperature is approximately in the range of from 20° to 200° C., preferably from 100° to 150° C., and the drying time approximately in the range of from 5 minutes to 48 hours, preferably from 10 to 60 minutes.

In the manner described above, the treatment for divestiture of lubricity is performed on part of the resin coating layer according with this invention.

In the present invention, the medical device furnished as an outer surface thereof with the substrate which is possessed of the resin coating partly treated for divestiture of lubricity as described above, on being wetted with the water type bodily humor, acquires on the surface thereof such low frictional resistance as required while the medical device is being inserted into the body, slid on the body tissues, or retained in the body, for example.

The medical devices to be produced by the present invention, therefore, include the following medical devices which are provided on the surface thereof with a coating layer contemplated by the present invention.

1) Catheters of the category represented by gastric tract catheter, alimentary catheter, and ED (alimentation via artificial passage) tube and adapted to be passed through the mouth or nose and inserted into or retained in the digestive tract.

2) Catheters of the category represented by tubes and cuffs in oxygen catheter, oxygen cannula, and intratracheal tube, a tube and a cuff in a tracheotomy tube, and an intratracheal aspirating tube and adapted to be passed through the mouth or nose and inserted into or retained in the air tube or trachea.

3) Catheters of the catogory represented by catheters and balloons in urethral catheter, urinating catheter, and balloon catheter and adapted to be inserted into or retained in the urethra or ureta.

4) Catheters of the catogory represented by aspiration catheter, excretion catheter, and rectal catheter and adapted to be inserted into or retained in various body cavities and tissues.

5) Catheters of the catogory represented by indwelling needle, IVH catheter, thermodilution catheter, angiographic catheter, PTCA grade catheter dilator, and introducer and adapted to be inserted into or retained in the blood vessels. Shells such as of guide wires and stylets for use with the aforementioned catheters are embraced in this category.

6) Surfaces of medical devices such as the outer surface of an endoscope which are required to offer only low frictional resistance during insertion or slide or during retention in the body.

Now, the present invention will be described more specifically below with reference to working examples of the invention.

The medical devices which are designed to be inserted into the body and moved to and operated at the region aimed at are represented by catheters. The catheters have guide wires as a guiding means.

Here, the effect of the present invention will be demonstrated below, with catheters as one embodiment.

EXAMPLE 1

A thermoplastic polyurethane resin (produced by The Dow Chemical Company and marketed under trademark designation of "Pellethane 2363-65D") having tungsten powder blended therewith in a proportion of 40% by weight was extrusion molded to produce a catheter tube of the 5Fr. size (1.67 mm in outside diameter and 1.1 mm in inside diameter). This product will be designated as a catheter tube No. 1. This catheter tube was immersed for 1-10 seconds in tetrahydrofuran (hereinafter referred to simply as "THF") and then dried at 25° C.

Then, polyvinyl chloride (polymerization degree 2,000) (hereinafter referred to briefly as "PVC") was dissolved in THF to prepare a 5 wt % PVC/THF solution. In this solution, 4,4-diphenylmethane diisocyanate (hereinafter referred to briefly as "MDI") was dissolved in a proportion of 6% by weight. The catheter tube was immersed for 1-10 minutes in the resultant solution and then dried at 25° C.

Further, the catheter tube was immersed in a THF 1 wt % methylvinyl ether-maleic anhydride copolymer (produced by G.A.F. Corp. and marketed under trademark designation of "GANTREZ AN-169") solution for 1-10 minutes and then dried at about 60° C.

In hot water kept at about 60° C., 0.1% by weight of NaCl and 0.05% by weight of NaHCO$_3$ were dissolved. The catheter tube was immersed for 30-120 seconds in the produced hot aqueous solution, washed with hot water, and dried at normal room temperature. The catheter tube consequently produced with a lubricant resin coating formed on the entire surface thereof will be designated as a catheter tube No. 2.

Further, the catheter tube No. 2 was immersed in a 1 wt % MDI/THF solution for five seconds, left drying in draft, and dried by heating at 100° to 150° C. for 10-60 minutes, to give rise to a catheter tube No. 3 having the entire surface thereof divested of lubricity.

Then, as illustrated in the figure a guide wire 2 was inserted into a bent tube 5 of PVC having an inside diameter of 3 mm.

The PVC tube 5 had an overall length of 450 mm and consisted of four straight parts 80 mm in length (See the dimension X in the drawing FIGURE). and three bent parts having a radius of curvature of 15 mm and including an angle of about 80 degrees and arranged in an undulating pattern as illustrated in the diagram.

The guide wire 2 consisted of a Ni-Ti core metal 0.5 mm in outside diameter and a sheath of a thermoplastic polyurethane resin coating 0.89 mm in outside diameter. It had a lubricant resin coating formed on the entire surface thereof in entirely the same manner as in the catheter tube No. 2.

The three kinds of catheter tube, i.e. the untreated catheter tube No. 1, the catheter tube No. 2 having the lubricant resin coating formed on the entire surface thereof, and the cathether tube No. 3 having the entire surface thereof treated for divestiture of lubricity, were each inserted around the aforementioned guide wire 2.

Thus, the catheter tube 1 was inserted into the bent PVC tube 5 between the tube 5 and the core wire 2. The magnitude of the maximum resistance offered by the catheter tube 1 during this insertion was measured with a tensile tester (produced by Toyo Seiki K.K. and marketed under trademark designation of "Strograph M-50").

In this case, the interior of the PVC tube was filled with tap water and the insertion was made at a rate of 100 mm/min.

The results of the test were shown in Table 1.

TABLE 1

| Catheter tube | Resistance to insertion |
| --- | --- |
| No. 1 Untreated | 300 g |
| No. 2 Lubricant resin coating | 60 g |
| No. 3 Divested of lubricity | 400 g |

It is clearly noted from the results shown in Table 1 that the treatment for divestiture of lubricity conspicuously increased the resistance to insertion.

When the treatment for divesting the catheter tube of lubricity was limited to the basal part of the catheter tube necessary for manipulation, the finally produced catheter tube enjoyed highly satisfactory manipulability.

What is claimed is:

1. A medical device for insertion into a body, said medical device including a basal part for manipulating the medical device, said medical device comprising a substrate that is entirely coated with a hydrophilic polymer coating, the hydrophilic polymer coating on said basal part being treated with an isocyanate prepolymer to reduce hydrophilicity and to increase the frictional resistance and the manipulability of the basal part of the medical device without generating lubricity even when wetted with a liquid.

2. A medical device according to claim 1, wherein said hydrophilic polymer coating is a maleic anhydride type polymer.

3. A medical device according to claim 2, wherein said maleic anhydride type polymer is a partial alkyl ester of a methylvinyl ether-maleic anhydride copolymer.

4. A medical device according to claim 1, wherein said polymer coating is deposited by virtue of covalent bond with a reactive functional group present on the surface of said substrate.

5. A medical device according to claim 1, wherein said substrate is fabricated of an organic polymer.

6. A medical device according to claim 5, wherein said organic polymer is one member selected from the group consisting of polyvinyl chloride resin, polyurethane resin, polyamide latex, and polyesters.

7. A medical device for insertion into a body that includes a basal part for manipulating the medical device, said medical device comprising a substrate that is entirely coated with a partial alkyl ester of a methyl vinyl ether-maleic anhydride copolymer, the coating on said basal part being treated with an isocyanate prepolymer to reduce the hydrophilicity of the basal part and to increase the manipulability and frictional resistance of the basal part of the medical device without generating lubricity even when wetted with a liquid.

8. A medical device according to claim 7, wherein said medical device is a catheter.

* * * * *

UNITED STATES PATENT AND TRADEMARK OFFICE
CERTIFICATE OF CORRECTION

PATENT NO. : 5,229,211
DATED : July 20, 1993
INVENTOR(S) : Hiraku MURAYAMA et al It is certified that error appears in the above-indentified patent and that said Letters Patent is hereby corrected as shown below:

In Column 1, line 50, delete "reamining" and insert -- remaining --.
In Column 3, line 40, delete "preferably" and insert -- preferable --.
In Column 4, line 14, delete "object" and insert -- objects --.
In Column 9, line 59, after "angle", insert -- $\alpha$ (See Fig. 1) --.

Signed and Sealed this

Twenty-ninth Day of March, 1994

*Attest:*

BRUCE LEHMAN

*Attesting Officer*　　*Commissioner of Patents and Trademarks*